(12) United States Patent
Virtue et al.

(10) Patent No.: US 8,588,486 B2
(45) Date of Patent: Nov. 19, 2013

(54) APPARATUS AND METHOD FOR ISOLATING A REGION IN AN IMAGE

(75) Inventors: Patrick Michael Virtue, Waukesha, WI (US); Gopal B. Avinash, Menomonee Falls, WI (US); Zhongmin S. Lin, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 1187 days.

(21) Appl. No.: 12/487,166

(22) Filed: Jun. 18, 2009

(65) Prior Publication Data

US 2010/0322488 A1    Dec. 23, 2010

(51) Int. Cl.
*G06K 9/00*      (2006.01)

(52) U.S. Cl.
USPC ............................ 382/128; 382/130; 382/131

(58) Field of Classification Search
None
See application file for complete search history.

(56) References Cited

U.S. PATENT DOCUMENTS

| | | | |
|---|---|---|---|
| 7,507,968 B2 * | 3/2009 | Wollenweber et al. .. | 250/363.07 |
| 7,672,708 B2 * | 3/2010 | Roberts .................. | 600/410 |
| 2007/0167716 A1 * | 7/2007 | Kinahan et al. ........... | 600/407 |
| 2007/0191704 A1 * | 8/2007 | DeCharms ................ | 600/411 |
| 2008/0284781 A1 * | 11/2008 | Wenger .................... | 345/424 |
| 2008/0292194 A1 * | 11/2008 | Schmidt et al. ........... | 382/217 |
| 2009/0012383 A1 * | 1/2009 | Virtue et al. .............. | 600/407 |
| 2009/0034823 A1 * | 2/2009 | Christiansen et al. ...... | 382/133 |
| 2009/0136096 A1 | 5/2009 | Sirohey et al. | |
| 2009/0306496 A1 * | 12/2009 | Koo et al. ................ | 600/417 |

OTHER PUBLICATIONS

"De-Skulling the brain," http://godzilla.kennedykrieger.org/sw/medx/webhelp/Tutorials/tut08_Interactive_Segmentation.pdf.
Koivistoinen et al., "Comparison of Pattern Classification Methods in Segmentation of Dynamic PET Brain Images," Proceedings of the 6th Nordic Signal Processing Symposium—NORSIG 2004, Jun. 9-11, 2004, Espoo, Finland, pp. 73-76.
Mykkanen et al., "Automatic extraction of brain surface and mid-sagittal plane from PET images applying deformable models," http://www.cs.uta.fi/reports/pdf/A-2003-1.pdf, Jun. 2, 2003.
Smith, "BET—Brain/Non-Brain Segmentation," Feb. 25, 2005, http://www.fmrib.ox.ac.uk/analysis/techrep/tr04ss2/tr04ss2/node10.html.
Tohka et al., "Cluster analysis for brain PET image segmentation," http://www.turkupetcentre.net/modelling/workshop4/brainsegmentation.pdf.
Studholme et al., "Automated three-dimensional registration of magnetic resonance and positron emission tomography brain images by multiresolution optimization of voxel similarity measures," Medical Physics, vol. 24, No. 1, Jan. 1997, pp. 25-35.
Itti et al., "Robust Multimodality Registration for Brain Mapping," Wiley-Liss, Inc., Human Brain Mapping, vol. 5, 1997, pp. 3-17.
"Thresholding (image processing)," http://en.wikipedia.org/wiki/Thresholding_(image_processing).

* cited by examiner

*Primary Examiner* — Nancy Bitar
(74) *Attorney, Agent, or Firm* — Ziolkowski Patent Solutions Group, SC

(57) ABSTRACT

A system, method, and apparatus includes a computer readable storage medium with a computer program stored thereon having instructions that cause a computer to access a first anatomical image data set of an imaging subject acquired via a morphological imaging modality, access a functional image data set of the imaging subject acquired via a functional imaging modality, register the first anatomical image data set to the functional image data set, segment the functional image data set based on the functional image data set, define a binary mask based on the segmented functional image data set, and apply the binary mask to the first anatomical image data set to construct a second anatomical image data set and an image based thereon. The second anatomical image data set is substantially free of image data of the first anatomical image data set correlating to an area outside the region of physiological activity.

20 Claims, 3 Drawing Sheets

APPARATUS AND METHOD FOR ISOLATING A REGION IN AN IMAGE

BACKGROUND OF THE INVENTION

The present invention relates generally to the creation of an imaging data set and more particularly to the creation of an imaging data set that represents an isolated region or area of a subject.

Morphological image data, also known as anatomical or structural image data (as opposed to functional image data), often contains impressive detail. For example, morphological MR head image data often provides detailed information of the anatomical structure of the brain. In order to analyze or quantify portions or regions of the brain, segmentation of the morphological brain image data found in the head image data is often employed. However, head image data also often includes skull image data, and before such segmentation of the brain image data can occur, it is desirous to first isolate the brain image data from the skull image data. That is, in such an instance, it can be difficult to analyze or quantify brain tissue data before non-brain tissue data is segmented from brain tissue data. As such, a segmentation technique is often first employed to segment the brain tissue data from the non-brain tissue data such as skull data. Once segmented, the isolated brain tissue data allows for image-processing algorithms to more easily segment different tissues or regions within the brain and generate quantitative data from the morphological brain data. One example of quantitative brain data is the thickness of the cerebral cortex, which is of interest in studies related to dementia, migraines, and intelligence, among others.

The amount of detail in some morphological image data makes the data rich in information, but the detail can also make it difficult to segment out the regions of interest. For example, the level of detail represented in a morphological image data set can make it difficult to isolate brain detail from surrounding detail such as eyes, skull, and other surrounding tissues. These same details can also make it difficult to generate a 3D contour separating brain from non-brain tissue. Segmentation may be directly employed on such data sets, but this may be a computational and algorithmically difficult task. Similar difficulties arise when attempting to quantify other regions or areas, other than the brain, of a subject.

It would therefore be desirable to have a system and method capable of efficiently isolating regions of an imaging subject for later quantitation.

BRIEF DESCRIPTION OF THE INVENTION

In accordance with one aspect of the invention, a computer readable storage medium has a computer program stored thereon. The computer program includes instructions, which when executed by a computer, cause the computer to access a first anatomical image data set of an imaging subject acquired via a morphological imaging modality, access a functional image data set of the imaging subject acquired via a functional imaging modality that images at least one biological process, register the first anatomical image data set to the functional image data set, segment the functional image data set based on a region of physiological activity of the functional image data set, define a binary mask based on the segmented functional image data set, apply the binary mask to the first anatomical image data set to construct a second anatomical image data set, and construct an image based on the second anatomical data set. The second anatomical image data set is substantially free of image data of the first anatomical image data set correlating to an area outside the region of physiological activity.

In accordance with another aspect of the invention, an image reconstruction method includes obtaining a first data set of imaging data of an anatomical region of an object acquired from the object via a morphological imaging modality, obtaining a second data set acquired from the object via a functional imaging modality. The second data set includes imaging data of at least one biological process of the object. The method also includes registering the first data set to the second data set, segmenting the second data set to produce a third data set having a masking data set registered to the first data set, producing a fourth data set from the first data set based on the masking data set, constructing an image from the fourth data set, and quantifying a region in the image. The fourth data set is a subset of the first data set.

In accordance with yet another aspect of the invention, a method includes registering a first data set acquired from an imaging subject via a morphological imaging modality to a second data set acquired from the imaging subject via a functional imaging modality, segmenting the second data set to create an imaging mask registered to the first data set. The imaging mask includes an area corresponding to physiological activity data in the second data set. The method also includes creating a third data set based on the imaging mask, quantifying a region of the imaging subject based on the third data set to determine a quantitative value of the region, and displaying the quantitative value to a user. The third data set includes data from the first data set, but is substantially free of data from the first data set that correlates to data outside the area.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 1:
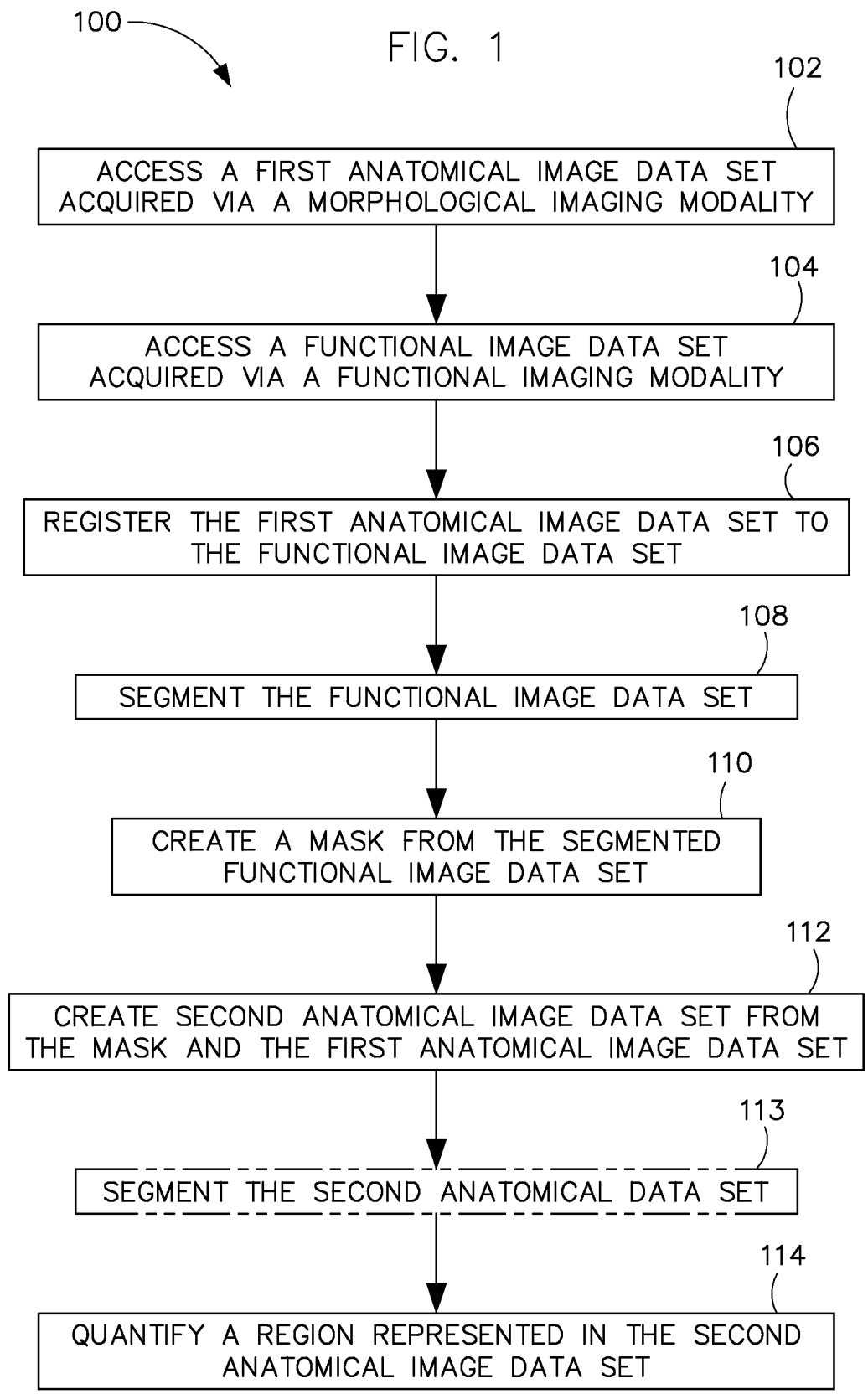
FIG. 1 is a flowchart depicting a technique for carrying out an embodiment of the invention.

Referring to FIG. 1, a flowchart depicting an imaging technique 100 is shown according to an embodiment of the invention. Technique 100 begins with block 102, where a first anatomical image data set acquired from an imaging subject is accessed or obtained. The first anatomical image data set is an anatomical data set acquired via an anatomical or morphological imaging modality. The morphological imaging modality may be, for example, a magnetic resonance (MR) imaging modality or a computed tomography (CT) imaging modality. An anatomical image data set acquired via other morphological imaging modalities is also contemplated.

Generally, morphological imaging modalities or apparatuses output anatomical or structural image data. A morphological imaging modality is in contrast to a functional imaging modality or apparatus such as, for example, a functional MR imaging (fMRI) modality, a positron emission tomography (PET) imaging modality, or a nuclear medicine imaging modality. Functional imaging modalities image functional processes (i.e., physiological activity) of a subject. Often, image data acquired via a functional imaging modality provides images depicting a strong contrast between regions with and without a particular physiological activity. It is noted that a combination of both morphological and functional imaging modalities may be embodied in one "apparatus." For example, an apparatus may include both CT imaging capabilities and PET imaging capabilities.

After accessing the first anatomical image data set acquired via a morphological imaging modality, process control proceeds to block 104, where a functional image data set acquired from the imaging subject is accessed or obtained. The functional image data set is acquired via a functional imaging modality such as fMRI or PET.

Though FIG. 1 depicts accessing the first anatomical image data set before the functional image data set, it is contemplated that the functional image data set may be accessed before the first anatomical image data set.

After accessing the functional image data set, process control proceeds to block 106, where the functional data set is registered to the first anatomical image data set. Registering the anatomical and functional image data sets together aligns the anatomical and functional image data sets in the same coordinate system. Accordingly, one or more areas or regions of the subject that are represented in both the first anatomical image data set and the functional image data set are registered to each other.

Proceeding to block 108, the functional image data set is then segmented to isolate at least one region or area of physiologic activity. As such, the segmentation is based on physiological activity represented in the functional image data set. For example, the functional image data set may have been acquired via a PET imaging modality. Further, the functional image data set may, for example, include data that represents the brain and skull of the imaging subject. If the PET imaging modality, for example, includes consumption of glucose in the brain, the portions of the brain that consume glucose will be separately identifiable in the functional image data set from regions where there is no glucose consumption. In one embodiment, areas where glucose consumption occurs (e.g., the brain) will have greater signal values than areas without glucose consumption (e.g., the skull). In such an instance, segmentation may be implemented to segment glucose producing areas or regions from non-glucose producing regions.

Any suitable type of segmentation may be implemented. For example, segmentation may include thresholding based on one or more threshold values compared with the signal values of the functional image data set, where one or more threshold values are automatically chosen by a computer and/or chosen by a user. In one instance, a computer or processor may automatically choose an initial threshold to be used for thresholding, and a user may later choose another threshold to "fine-tune" the thresholding segmentation. It is also contemplated that the one or more threshold values may be solely determined by the computer/processor or the user. A computer such as computer system 192 of FIG. 2 may be used to carry out technique 100 of FIG. 1. However, it is contemplated that another computer or processor may be used to carry out embodiments of the invention. The computer or processor may be coupled to one of the imaging modalities (e.g., a morphological imaging modality or a functional imaging modality), or the computer or processor may be a stand-alone unit that receives image data via inputs.

Referring back to FIG. 1, other segmentation techniques such as erosion, dilation, and/or island removal may be implemented instead of implementing a thresholding segmentation. It is yet further contemplated that a combination of these segmentation techniques may be implemented.

Since the functional image data set is registered to the first anatomical image data sets, technique 100 allows for a visual interactive segmentation process. That is, a user can be presented with fused multi-planar reformat views (i.e., a view of the functional image over the first anatomical image) and be allowed to manipulate the functional image if any "fine-tuning" is needed until the functional image is visually aligned with the first anatomical image. The user can then be allowed to manipulate the segmentation process to aid in the isolation of the particular physiologic activity. A connected components algorithm can then be implemented by the computer to remove extraneous regions that are not connected to the region or area of interest.

After segmentation, process control proceeds to block 110, where a mask such as a binary mask is created from the segmented functional image data set. That is, for example, some regions represented in the segmented functional image data set may be assigned values of zero, and other regions may be assigned values of one. Accordingly a mask comprising ones and zeros is produced through segmentation. Since the mask is produced from the functional image data set, which is registered to the first anatomical image data set, the mask is also registered to the first anatomical image data set.

In an example where the functional image data set was acquired via a PET imaging modality that depicts glucose consumption, the glucose consuming areas (i.e., the areas of physiologic activity) represented in the segmented functional data set can be assigned a value of one, whereas the non-glucose consuming areas represented in the functional image data set may be assigned a value of zero. It is contemplated that other values may instead be assigned to these regions. Nonetheless, the segmented functional image data set is converted to an imaging mask. It is contemplated that segmentation and mask creation could be accomplished as a combined process, rather than a process that first includes segmentation and then creates a mask therefrom.

After creating or producing the imaging mask, process control proceeds to block 112, where a second anatomical image data set is produced via application of the imaging mask to the first anatomical image data set (the first anatomical image data set being registered to the imaging mask) such that a region of the imaging subject in the first anatomical image data set may be isolated from areas outside the region. For example, if an area in a subject's head were imaged via an MR imaging modality (i.e., a morphological imaging modality) and also via a PET imaging modality (i.e., a functional imaging modality), a mask registered to the MR image data set may be used to isolate, for example, the brain from the skull of the subject. In other words, in the example above, where a PET imaging modality that depicts glucose consumption was used to create the functional image data set, a computer or processor may create a second anatomical image data set that includes data from the first anatomical data set that correlates to the glucose consuming areas represented in the imaging mask. Further, the computer or processor can cause the second anatomical data set to be substantially void of data from the first anatomical image data set that correlates to the non-glucose consuming areas represented in the imaging mask. Accordingly, by using the mask that has been registered to the first anatomical data set, a second anatomical image data set that represents an isolated brain region of the subject can be created from the first anatomical image data set for example.

It is also contemplated that, rather than isolating a brain region, as in the example above, the imaging mask registered to the first anatomical data set may be used to isolate the skull region of the subject. In such an instance, a computer or processor creates a second anatomical image data set from the first anatomical image data set that is substantially free of data from the first anatomical image data set that correlates to glucose consuming areas represented in the imaging mask. As such, an image of the isolated skull region may be constructed from the second anatomical image data set based on the imaging mask.

The examples set forth above illustrate embodiments of the invention. However, other embodiments are also contemplated. For example, embodiments of the invention may be implemented to isolate regions of the subject other than brain or skull regions such as the heart or the liver. Further, embodiments of the invention allow for masks to be created from functional image data sets other than PET image data sets. Likewise, embodiments of the invention allow for images of isolated areas to be created from anatomical image data sets other than MR image data sets.

In one embodiment, after isolating the region or area in the imaging subject, process control proceeds to block 113 (shown in phantom), where the second anatomical image data set is segmented. It is contemplated that this additional segmentation may be implemented to further define the region or area. For example, dilation and/or erosion techniques may be used to further define the region. Accordingly extraneous portions of the region may be removed or, in addition to or in the alternative, portions may be added to the region. In either case, a more robust second anatomical data set or image may be created through additional segmentation.

In addition to, or instead of, the thresholding, erosion, and dilation segmenting techniques discussed above with respect to blocks 108 and 113, other segmentation techniques may be implemented at blocks 108 and 113. For example, other morphological operators, region growing, clustering, histogram-based, edge detection, level set, graph partitioning, watershed transformation, model-based, multi-scale, and or/neural network segmenting techniques may be implemented. In addition, still other segmenting techniques not discussed may be implemented.

After isolating the region or area in the imaging subject, whether or not the second data set was segmented, process control proceeds to block 114, where the isolated region or area, or portion(s) thereof, represented in the second anatomical data set is quantified or quantitated. For example, if an isolated brain region is represented in a second MR image data set (i.e., a second anatomical data set), a length, height, or area of the isolated brain may be determined. If the second MR image data set is a three-dimensional MR image data set, the volume of a brain may also be determined. Further, due to the detail often represented in MR data sets, the percentage of white and/or grey matter represented in the data set may also be determined or quantified. Still further, other types of quantitation are also envisioned such as a measure the thickness of the cerebral cortex (gray matter) to be used to study dementia in patients. Further segmentation of the resulting second anatomical image data set may be needed for particular types of quantitation.

Due to the ability to isolate regions or areas in an imaging subject, technique 100 allows for more accurate quantification of these regions or areas. For example, an anatomical image data set that represents a portion of an imaging sub-ject's head may include data that represents portions of the skull and the brain of the imaging subject. However, in such an anatomical data set it can be difficult to delineate a boundary between the skull and the brain. Accordingly, it may be difficult to quantify, for example, the skull portions or the brain portions represented in the complete anatomical image data set. Segmenting techniques may be implemented on the anatomical data set in an attempt to isolate the desired anatomical regions, but it can be computationally or algorithmically difficult to perform such segmentation on the anatomical data set itself. Technique 100, however, allows for segmentation to be performed on a functional image data set, which can be computationally or algorithmically less difficult than performing the same process on other data sets such as an anatomical image data set, and for the segmented functional image data set to be used for segmenting the anatomical image data set.

As such, according to technique 100, a mask can be created from the segmented functional image data set. Since, as depicted in technique 100, the mask is registered to the first anatomical image data set, such as an anatomical MR image data set, a desired isolated anatomical region or area of the first anatomical image data set may be represented in a second anatomical data set created from a combination of the mask and the first anatomical image data set. In other words, if the first anatomical image data set includes data of the brain and skull of an imaging subject, a second MR data set can be created that represents either the isolated skull or the isolated brain region of the imaging subject.

Figure 2:
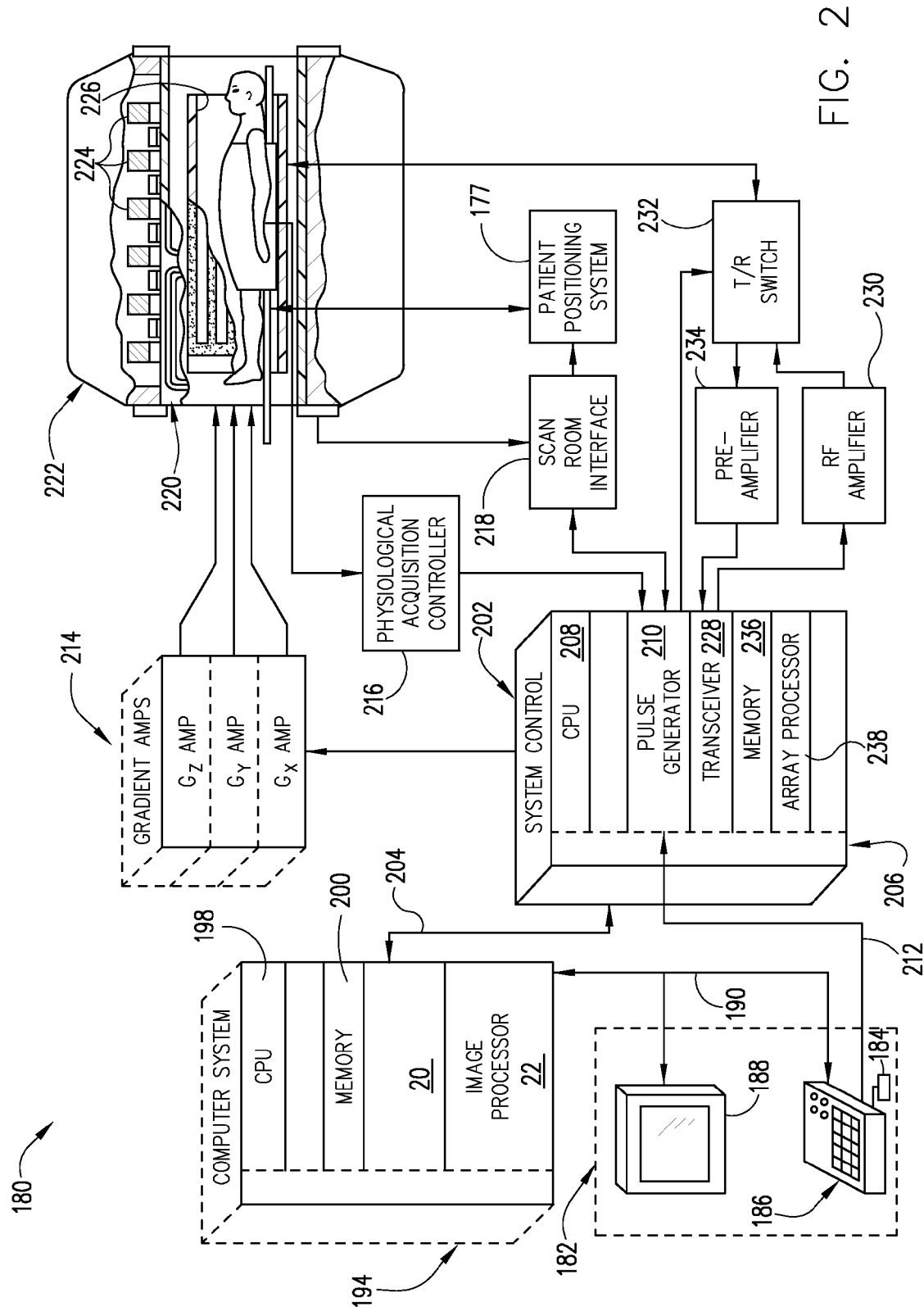
FIG. 2 is a schematic block diagram of an exemplary magnetic resonance (MR) imaging system for use with embodiments of the invention.

As discussed above, embodiments of the invention include accessing image data sets that may be acquired using a variety of imaging modalities. An exemplary imaging device or modality is depicted in FIG. 2, in which the major components of a magnetic resonance imaging (MRI) system 180 for acquiring an anatomical image data set. The operation of the system is controlled from an operator console 182 which includes a 184, a control panel 186, and a display screen 188. The console 182 communicates through a link 190 with a separate computer system 192 that enables an operator to control the production and display of images on the display screen 188. The computer system 192 includes a number of modules which communicate with each other through a backplane 194. These include an image processor module 196, a CPU module 198 and a memory module 200, known in the art as a frame buffer for storing image data arrays. The computer system 192 communicates with a separate system control 202 through a high speed serial link 204. The input device 184 can include a mouse, joystick, keyboard, track ball, touch activated screen, light wand, voice control, or any similar or equivalent input device, and may be used for interactive geometry prescription.

The system control 202 includes a set of modules connected together by a backplane 206. These include a CPU module 208 and a pulse generator module 210 which connects to the operator console 182 through a serial link 212. It is through link 212 that the system control 202 receives commands from the operator to indicate the scan sequence that is to be performed. The pulse generator module 210 operates the system components to carry out the desired scan sequence and produces data which indicates the timing, strength and shape of the RF pulses produced, and the timing and length of the data acquisition window. The pulse generator module 210 connects to a set of gradient amplifiers 214, to indicate the timing and shape of the gradient pulses that are produced during the scan. The pulse generator module 210 can also receive patient data from a physiological acquisition controller 216 that receives signals from a number of different sensors connected to the patient, such as ECG signals from electrodes attached to the patient. And finally, the pulse generator module 210 connects to a scan room interface circuit 218 which receives signals from various sensors associated with the condition of the patient and the magnet system. It is also through the scan room interface circuit 218 that a patient positioning system 177 receives commands to move the patient to the desired position for the scan.

The gradient waveforms produced by the pulse generator module 210 are applied to the gradient amplifier system 214 having Gx, Gy, and Gz amplifiers. Each gradient amplifier excites a corresponding physical gradient coil in a gradient coil assembly generally designated 220 to produce the magnetic field gradients used for spatially encoding acquired signals. The gradient coil assembly 220 forms part of a magnet assembly 222 which includes a polarizing magnet 224 and a whole-body RF coil 226. A transceiver module 228 in the system control 202 produces pulses which are amplified by an RF amplifier 230 and coupled to the RF coil 226 by a transmit/receive switch 232. The resulting signals emitted by the excited nuclei in the patient may be sensed by the same RF coil 226 and coupled through the transmit/receive switch 232 to a preamplifier 234. The amplified MR signals are demodulated, filtered, and digitized in the receiver section of the transceiver 228 transmit/receive switch 232 is controlled by a signal from the pulse generator module 210 to electrically connect the RF amplifier 230 to the coil 226 during the transmit mode and to connect the preamplifier 234 to the coil 226 during the receive mode. The transmit/receive switch 232 can also enable a separate RF coil (for example, a surface coil) to be used in either the transmit or receive mode.

The MR signals picked up by the RF coil 226 are digitized by the transceiver module 228 and transferred to a memory module 236 in the system control 202. A scan is complete when an array of raw k-space data has been acquired in the memory module 236. This raw k-space data is rearranged into separate k-space data arrays for each image to be reconstructed, and each of these is input to an array processor 238 which operates to Fourier transform the data into an array of image data. This image data is conveyed through the serial link serial link 204 to the computer system 192 where it is stored in memory. In response to commands received from the operator console 182, this image data may be archived in long term storage or it may be further processed by the image processor 196 and conveyed to the operator console 182 and presented on the display 188.

In addition to creating an anatomical imaging data set, MRI system 180 may also be programmed to perform technique 100. That is, computer system 192 may be configured or programmed to access an anatomical image data set acquired via MRI system 180 together with a functional image data set acquired via MRI system 180 (if MRI system 180 is also used as an fMRI) or via another functional imaging modality and to use those image data sets for performing the steps of technique 100.

Figure 3:
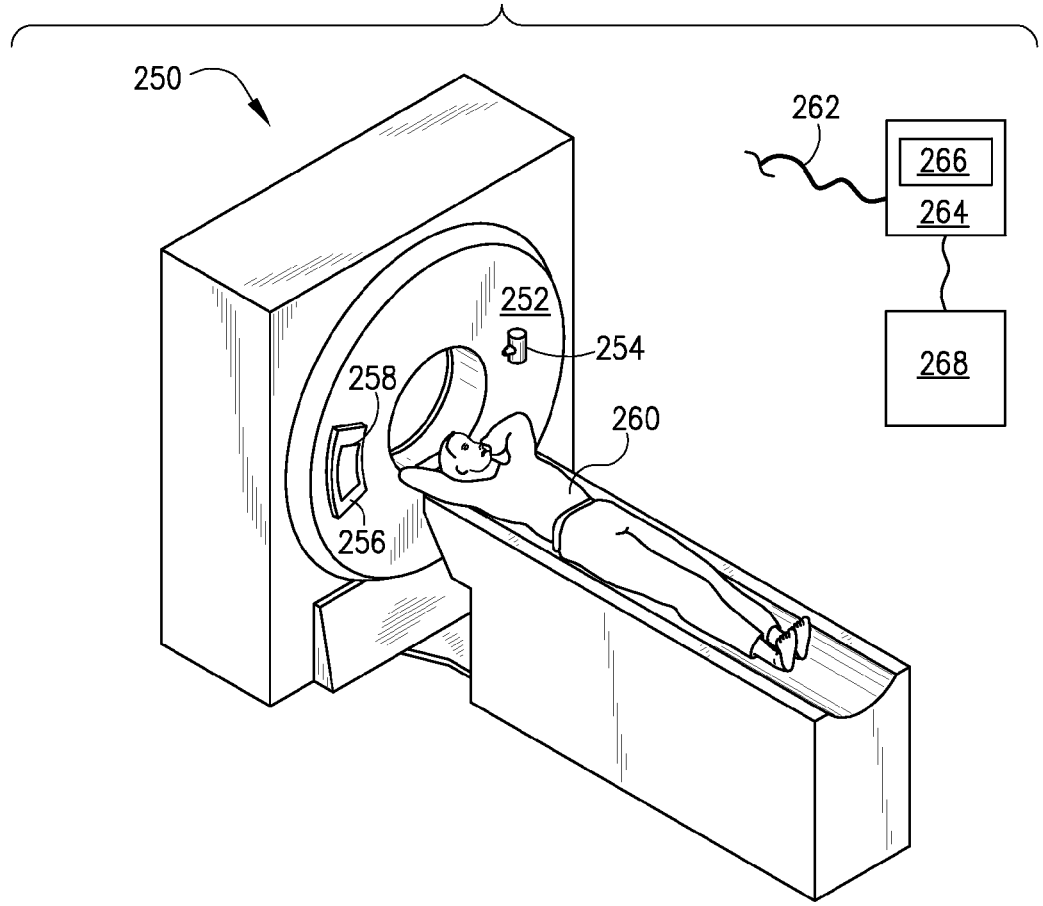
FIG. 3 is a schematic diagram of an exemplary computed tomography (CT) system for use with embodiments of the invention.

Referring now to FIG. 3, an exemplary CT system 250 that may be used in accordance with embodiments of the invention is shown. CT system 250 may be used as a morphological or as a functional imaging modality that produces anatomical data sets or functional data sets, respectively. CT imaging system 250 includes a gantry 252 representative of a "third generation" CT scanner. Gantry 252 has an x-ray source 254 that projects a beam of x-rays toward a detector assembly or collimator 256 on the opposite side of the gantry 252. Detector assembly 256 is formed by a plurality of detectors (not shown) and data acquisition systems (DAS) 258 The plurality of detectors sense the projected x-rays that pass through a medical patient 260, and DAS 258 converts the data to digital signals for subsequent processing. Each detector of detector assembly 256 produces an analog electrical signal that represents the intensity of an impinging x-ray beam and hence the attenuated beam as it passes through the patient 260. During a scan to acquire x-ray projection data, gantry 252 and the components mounted thereon rotate about a center of rotation.

An image reconstructor (not shown) receives sampled and digitized x-ray data from the DAS and performs high speed reconstruction. The reconstructed image is applied as an input, via a serial link 262, to a computer 264 which stores the image in a mass storage device 266.

Computer 260 also receives commands and scanning parameters from an operator. An associated display 268 allows the operator to observe the reconstructed image and other data from computer 264. In addition to creating an anatomical and/or a functional imaging data set, CT system 250 may also be programmed to perform technique 100. That is, computer 264 may be configured or programmed to access, for example, an anatomical image data set acquired via MRI system 180 of FIG. 2 or an anatomical data set acquired via CT system 250 of FIG. 3 together with a functional image data set acquired via MRI system 180 of FIG. 2 (if MRI system 180 is used as an fMRI), CT system 250 of FIG. 3, or via another functional imaging modality such as PET system 270 of FIG. 4 below and to use those image data sets for performing the steps of technique 100.

Figure 4:
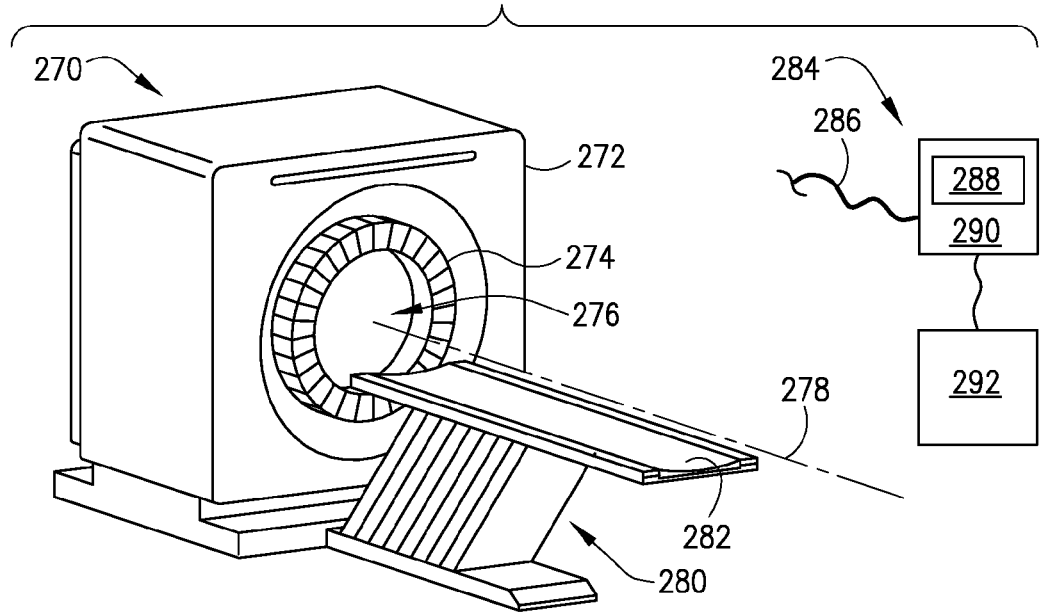
FIG. 4 is a schematic diagram of an exemplary positron emission tomography (PET) imaging system for use with embodiments of the invention.

Referring now to FIG. 4, an exemplary PET system 270 that may be used in accordance with embodiments of the invention is shown. PET system 270 may be used as a functional imaging modality that produces functional image data sets. PET scanner 270 includes a gantry 272 which supports a detector ring assembly 274 about a central opening or bore 276. Detector ring assembly 274 is circular in shape, and is made up of multiple detector rings (not shown) that are spaced along a central axis 278 to form a cylindrical detector ring assembly. A patient table 280 is positioned in front of gantry 272 and is aligned with a central axis 278 of the detector ring assembly 274. A patient table controller (not shown) moves a table bed 282 into bore 276 in response to commands received from a computer or operator work station 284 through a serial communications link 286. Work station 284 includes a computer readable storage medium 288, a processor 290, and a display 292, and a user can control PET system 270 via work station 284.

In addition to creating a functional imaging data set, PET system 270 may also be programmed to perform technique 100. That is, work station 284 may be configured or programmed to access, for example, a functional image data set acquired via PET system 270 and an anatomical image data set acquired via MRI system 180 of FIG. 2 or CT system 250 of FIG. 3 and to use those image data sets for performing the steps of technique 100.

Technique 100 of FIG. 1 may be implemented with anatomical image data sets acquired via morphological imaging modalities other than MR and CT imaging modalities. Likewise, technique 100 may be implemented with functional image data sets acquired via functional imaging modalities other than PET, MR, or CT imaging modalities.

A technical contribution for the disclosed method, apparatus, and system is that it provides for a computer implemented method, apparatus, and system of isolating a region in an image.

In accordance with one embodiment, a computer readable storage medium has a computer program stored thereon. The computer program includes instructions, which when executed by a computer, cause the computer to access a first anatomical image data set of an imaging subject acquired via a morphological imaging modality, access a functional image data set of the imaging subject acquired via a functional imaging modality that images at least one biological process, register the first anatomical image data set to the functional image data set, segment the functional image data set based on a region of physiological activity of the functional image data set, define a binary mask based on the segmented functional image data set, apply the binary mask to the first anatomical image data set to construct a second anatomical image data set, and construct an image based on the second anatomical data set. The second anatomical image data set is substantially free of image data of the first anatomical image data set correlating to an area outside the region of physiological activity.

In accordance with another embodiment, a method includes registering a first data set acquired from an imaging subject via a morphological imaging modality to a second data set acquired from the imaging subject via a functional imaging modality, segmenting the second data set to create an imaging mask registered to the first data set. The imaging mask includes an area corresponding to physiological activity data in the second data set. The method also includes creating a third data set based on the imaging mask, quantifying a region of the imaging subject based on the third data set to determine a quantitative value of the region, and displaying the quantitative value to a user. The third data set includes data from the first data set, but is substantially free of data from the first data set that correlates to data outside the area.

In accordance with yet another embodiment, a method includes registering a first data set acquired from an imaging subject via a morphological imaging modality to a second data set acquired from the imaging subject via a functional imaging modality, segmenting the second data set to create an imaging mask registered to the first data set. The imaging mask includes an area corresponding to physiological activity data in the second data set. The method also includes creating a third data set based on the imaging mask, quantifying a region of the imaging subject based on the third data set to determine a quantitative value of the region, and displaying the quantitative value to a user. The third data set includes data from the first data set, but is substantially free of data from the first data set that correlates to data outside the area.

The present invention has been described in terms of the preferred embodiments, and it is recognized that equivalents, alternatives, and modifications, aside from those expressly stated, are possible and within the scope of the appending claims.

What is claimed is:

1. A non-transitory computer readable storage medium having stored thereon a computer program comprising instructions which when executed by a computer cause the computer to:
   access a first anatomical image data set of an imaging subject acquired via a morphological imaging modality;
   access a functional image data set of the imaging subject acquired via a functional imaging modality that images at least one biological process;
   register the first anatomical image data set to the functional image data set;
   segment the functional image data set based on a region of physiological activity of the functional image data set;
   define a binary mask based on the segmented functional image data set;
   apply the binary mask to the first anatomical image data set to construct a second anatomical image data set, wherein the second anatomical image data set is substantially free of image data from the first anatomical image data set correlating to an area outside the region of physiological activity; and
   construct an image based on the second anatomical image data set.

2. The computer readable storage medium of claim 1 wherein the instructions further cause the computer to:
   quantify the region of the imaging subject based on the second anatomical image data set; and
   display the quantification to a user.

3. The computer readable storage medium of claim 2 wherein the instructions further cause the computer to quantify the region cause the computer to at least one of:
   determine an area of the region; and
   determine a volume of the region.

4. The computer readable storage medium of claim 1 wherein the instructions that cause the computer to segment the functional image data set cause the computer to apply a thresholding to data of the functional image data set.

5. The computer readable storage medium of claim 4 wherein the instructions further cause the computer to receive a threshold value from a user input, and wherein instructions that cause the computer to apply the thresholding cause the computer to apply the thresholding based on the threshold value.

6. The computer readable storage medium of claim 1 wherein the instructions further cause the computer to apply a set of morphological operations to the second anatomical image data set.

7. The computer readable storage medium of claim 1 wherein the morphological imaging modality comprises a magnetic resonance (MR) imaging modality and the functional imaging modality comprises a positron emission tomography (PET) imaging modality.

8. An image reconstruction method comprising:
   obtaining a first data set acquired from an object via a morphological imaging modality, the first data set comprising imaging data of an anatomical region of the object;
   obtaining a second data set acquired from the object via a functional imaging modality, the second data set comprising imaging data of at least one biological process of the object;
   registering the first data set to the second data set;
   segmenting the second data set to produce a third data set comprising a masking data set registered to the first data set;
   producing a fourth data set from the first data set based on the masking data set, wherein the fourth data set is a subset of the first data set substantially free of image data correlating to an area outside a region of physiological activity;
   constructing an image from the fourth data set; and
   quantifying a region in the image.

9. The method of claim 8 wherein quantifying the region in the image comprises determining an area of the region.

10. The method of claim 8 wherein quantifying the region in the image comprises determining a volume of the region.

11. The method of claim 8 further comprising segmenting the fourth data set prior to constructing the image from the fourth data set.

12. The method of claim 8 wherein segmenting the second data set comprises thresholding the second data set based on a threshold value input by a user.

13. The method of claim 12 wherein segmenting the second data set further comprises implementing an island removal technique.

14. A method comprising:
acquiring a first data set comprising anatomical data of an object via a morphological imaging modality;
acquiring a second data set comprising a biological process of the object via a functional imaging modality;
registering the first data set to the second data set;
segmenting the second data set to create an imaging mask registered to the first data set, the imaging mask comprising an area corresponding to physiological activity data in the second data set;
creating a third data set based on the imaging mask, the third data set comprising data from the first data set, wherein the third data set is substantially free of data from the first data set that correlates to data outside the area corresponding to physiological activity data;
quantifying a region of the imaging subject based on the third data set to determine a quantitative value of the region;
construct an image based on the third data set; and displaying the quantitative value to a user.

15. The method of claim 14 wherein quantifying the region comprises determining an area of the region.

16. The method of claim 14 wherein quantifying the region comprises determining a volume of the region, wherein the third data set is a three-dimensional image data set.

17. The method of claim 14 wherein the morphological imaging modality is a magnetic resonance imaging modality, and wherein the functional imaging modality is a positron emission tomography imaging modality.

18. The method of claim 14 wherein segmenting the second data set comprises at least one of thresholding the second data set, applying a morphological operator technique to the second data set, and applying a region growing technique to the second data set.

19. The method of claim 18 wherein thresholding the second data set comprises thresholding the second data set based on a first threshold value determined by a computer and a second threshold value determined by a user.

20. The method of claim 14 further comprising segmenting the third data set prior to quantifying the region of the imaging subject.

* * * * *